(12) United States Patent
Arcidi

(10) Patent No.: US 9,445,899 B2
(45) Date of Patent: Sep. 20, 2016

(54) METHOD AND APPARATUS FOR MITRAL VALVE ANNULOPLASTY

(71) Applicant: Joseph M. Arcidi, Fenton, MI (US)

(72) Inventor: Joseph M. Arcidi, Fenton, MI (US)

( * ) Notice: Subject to any disclaimer, the term of this patent is extended or adjusted under 35 U.S.C. 154(b) by 371 days.

(21) Appl. No.: 13/844,117

(22) Filed: Mar. 15, 2013

(65) Prior Publication Data
US 2014/0277406 A1 Sep. 18, 2014

Related U.S. Application Data

(60) Provisional application No. 61/692,100, filed on Aug. 22, 2012.

(51) Int. Cl.
*A61F 2/24* (2006.01)

(52) U.S. Cl.
CPC ........... *A61F 2/2466* (2013.01); *A61F 2/2445* (2013.01); *A61F 2/2442* (2013.01); *A61F 2/2451* (2013.01); *A61F 2220/0033* (2013.01); *A61F 2250/001* (2013.01); *A61F 2250/0007* (2013.01)

(58) Field of Classification Search
CPC .. A61F 2/2442; A61F 2/2451; A61F 2/2466; A61F 2/2445; A61F 2/0007; A61F 2/001; A61F 2220/0033
See application file for complete search history.

(56) References Cited

U.S. PATENT DOCUMENTS

| | | | |
|---|---|---|---|
| 5,509,428 A | 4/1996 | Dunlop | |
| 5,935,120 A | 8/1999 | Williams et al. | |
| 6,540,782 B1 | 4/2003 | Snyders | |
| 6,718,985 B2 | 4/2004 | Hlavka et al. | |
| 6,945,978 B1 | 9/2005 | Hyde | |
| 6,986,775 B2 | 1/2006 | Morales et al. | |
| 7,213,601 B2 | 5/2007 | Stevens et al. | |
| 7,311,728 B2 | 12/2007 | Solem et al. | |
| 7,316,706 B2 | 1/2008 | Bloom et al. | |
| 7,381,210 B2 | 6/2008 | Zarbatany et al. | |
| 7,503,932 B2 | 3/2009 | Mathis et al. | |
| 7,544,206 B2 | 6/2009 | Cohn | |
| 7,569,062 B1 | 8/2009 | Kuehn et al. | |
| 7,608,091 B2 | 10/2009 | Goldfarb et al. | |
| 7,655,040 B2 | 2/2010 | Douk et al. | |
| 7,666,224 B2 | 2/2010 | Vidlund et al. | |
| 7,753,924 B2 | 7/2010 | Starksen et al. | |
| 7,758,596 B2 | 7/2010 | Oz et al. | |
| 7,758,637 B2 | 7/2010 | Starksen et al. | |
| 7,837,728 B2 | 11/2010 | Nieminen et al. | |
| 7,887,552 B2 | 2/2011 | Bachman | |
| 7,918,865 B2 | 4/2011 | Liddicoat et al. | |
| 7,993,396 B2 | 8/2011 | McCarthy | |
| 8,029,518 B2 | 10/2011 | Goldfarb et al. | |
| 8,092,525 B2 | 1/2012 | Eliasen et al. | |
| 8,108,034 B2 | 1/2012 | Patangay et al. | |

(Continued)

*Primary Examiner* — Robert Lynch
(74) *Attorney, Agent, or Firm* — Brooks Kushman P.C.

(57) ABSTRACT

A method for mitral valve annuloplasty includes inserting a catheter apparatus across an aortic valve, the catheter apparatus including a tissue penetration member having a distal fixation end. The method further includes penetrating an aortomitral continuity and tissue of a fibrous trigone with the catheter apparatus from a left ventricular outflow tract beneath the aortic valve, and advancing the catheter apparatus along annular tissue of a mitral valve annulus. The distal fixation end is deployed to engage the annular tissue, the tissue penetration member is retracted within the catheter apparatus to compress the annular tissue a desired distance for reduction of the annular tissue, and the retracted tissue penetration member is secured to anchor the annular tissue reduction.

14 Claims, 17 Drawing Sheets

(56) References Cited

U.S. PATENT DOCUMENTS

| | | |
|---|---|---|
| 8,142,493 B2 | 3/2012 | Spence et al. |
| 8,163,010 B1 | 4/2012 | Hausen et al. |
| 8,172,856 B2 | 5/2012 | Eigler et al. |
| 8,187,299 B2 | 5/2012 | Goldfarb et al. |
| 8,197,464 B2 | 6/2012 | Krever et al. |
| 8,216,254 B2 | 7/2012 | McLean et al. |
| 8,216,302 B2 | 7/2012 | Wilson et al. |
| 2003/0078654 A1 | 4/2003 | Taylor et al. |
| 2003/0114901 A1 | 6/2003 | Loeb et al. |
| 2005/0216039 A1 | 9/2005 | Lederman |
| 2005/0240249 A1 | 10/2005 | Tu et al. |
| 2006/0030882 A1 | 2/2006 | Adams et al. |
| 2006/0095025 A1 | 5/2006 | Levine et al. |
| 2006/0282161 A1* | 12/2006 | Huynh et al. ............ 623/2.11 |
| 2007/0027533 A1 | 2/2007 | Douk |
| 2007/0066863 A1 | 3/2007 | Rafiee et al. |
| 2007/0197919 A1 | 8/2007 | Krisch et al. |
| 2007/0203391 A1 | 8/2007 | Bloom et al. |
| 2007/0250161 A1 | 10/2007 | Dolan |
| 2008/0065205 A1 | 3/2008 | Nguyen et al. |
| 2009/0137968 A1 | 5/2009 | Rottenberg |
| 2009/0177277 A1* | 7/2009 | Milo ............ 623/2.36 |
| 2010/0094314 A1* | 4/2010 | Hernlund et al. ............ 606/139 |
| 2010/0094334 A1 | 4/2010 | Krever et al. |
| 2010/0160725 A1 | 6/2010 | Kiser et al. |
| 2012/0041548 A1 | 2/2012 | Crabtree |
| 2012/0123532 A1 | 5/2012 | Mathis |

* cited by examiner

METHOD AND APPARATUS FOR MITRAL VALVE ANNULOPLASTY

CROSS-REFERENCE TO RELATED APPLICATIONS

This application claims the benefit of U.S. provisional Application No. 61/692,100 filed Aug. 22, 2012, the disclosure of which is incorporated in its entirety by reference herein.

TECHNICAL FIELD

Embodiments relate to a method and apparatus for mitral valve annuloplasty, such as to correct mitral valve regurgitation.

BACKGROUND

A normal mitral heart valve, as viewed from the left atrium heart chamber, includes anterior and posterior mitral valve leaflets and the mitral valve annulus (FIG. 1A). The mitral annulus is the attachment point of the valve to the heart muscle and is composed of fibrous tissue. When the mitral heart valve develops leakage, clinically termed "mitral regurgitation" (FIG. 1B), it is associated with morbidity and mortality from congestive heart failure. Nearly all successful open-heart surgical methods to correct mitral valve regurgitation involve mitral valve annuloplasty, which involves reduction of the mitral valve annulus dimension or remodeling of the mitral valve annular shape. Surgical approaches to the mitral valve are invasive and carry significant risk, especially in sicker patients, and mitral annuloplasty can be difficult during conventional or even minimally invasive open-heart surgery, especially if the left atrium heart chamber is small in diameter.

A catheter-based approach to mitral valve annuloplasty would avoid surgical risk, but no catheter-based methods or devices for mitral valve annuloplasty have achieved safe, effective, durable, and reproducible correction of mitral regurgitation in tested clinical use. Previous methods with catheter-based devices for mitral valve annuloplasty have involved access to the mitral annulus through the left atrium, or through the left ventricular cavity adjacent to the chordae, or through the coronary sinus with juxtaposition to the mitral annulus. Previous methods which involve a retained foreign body in a heart chamber with a low-velocity of blood flow, such as the coronary sinus, the left atrium, or the inflow aspect of the left ventricle, may require life-long anticoagulation with its inherent complications.

SUMMARY

In one embodiment, a method for mitral valve annuloplasty is provided including inserting a catheter apparatus across an aortic valve, the catheter apparatus including a tissue penetration member having a distal fixation end. The method further includes penetrating an aortomitral continuity and tissue of a fibrous trigone with the catheter apparatus from a left ventricular outflow tract beneath the aortic valve, and advancing the catheter apparatus along annular tissue of a mitral valve annulus. The distal fixation end is deployed to engage the annular tissue, the tissue penetration member is retracted within the catheter apparatus to compress the annular tissue a desired distance for reduction of the annular tissue, and the retracted tissue penetration member is secured to anchor the annular tissue reduction.

In another embodiment, a method for mitral valve annuloplasty is provided including inserting a catheter apparatus across an aortic valve, the catheter apparatus including a tissue penetration member having a distal fixation end, the tissue penetration member surrounded by a sheath. The method further includes penetrating an aortomitral continuity and tissue of a fibrous trigone with the catheter apparatus from a left ventricular outflow tract beneath the aortic valve, and advancing the catheter apparatus along annular tissue of a mitral valve annulus. The sheath is retracted to deploy the distal fixation end and engage the annular tissue. The method further includes calibrating a desired distance for reduction of the annular tissue, retracting the tissue penetration member within the catheter apparatus to compress the annular tissue the desired distance, and deploying a grommet along the tissue penetration member to secure the retracted tissue penetration member and anchor the annular tissue reduction at the aortomitral continuity.

In another embodiment, a catheter apparatus for mitral valve annuloplasty is provided which includes a housing, and a retractable tissue penetration member disposed within the housing and having a distal fixation end configured to engage annular tissue of a mitral valve annulus in a deployed position. A retractable sheath surrounds the tissue penetration member and is operable to retract with respect to the tissue penetration member to provide the deployed position of the distal fixation end. A one-way grommet is disposed along the tissue penetration member for securing the tissue penetration member in a retracted position to anchor the annular tissue at a desired distance.

DETAILED DESCRIPTION

Figure 1A:
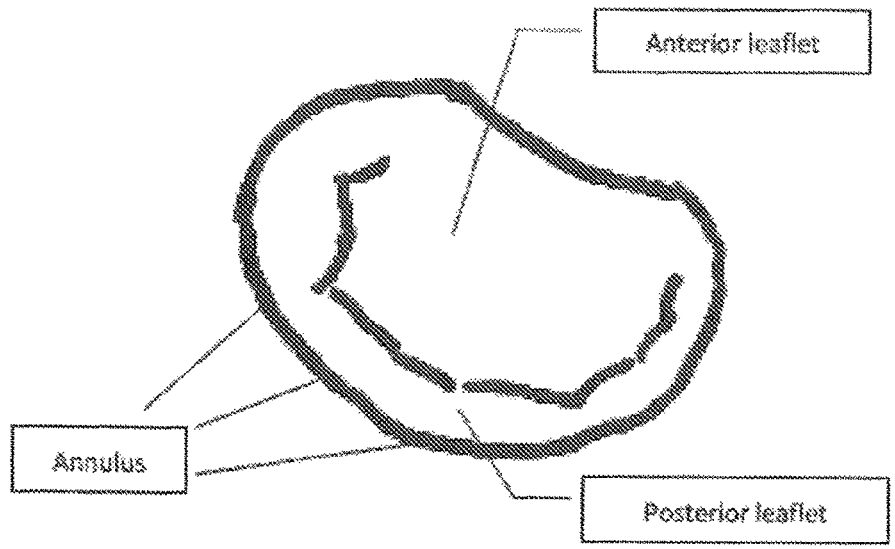
FIGS. 1A and 1B are illustrations of a normal mitral heart valve and a regurgitant mitral valve, respectively, as viewed from the left atrium heart chamber.
Figure 1B:
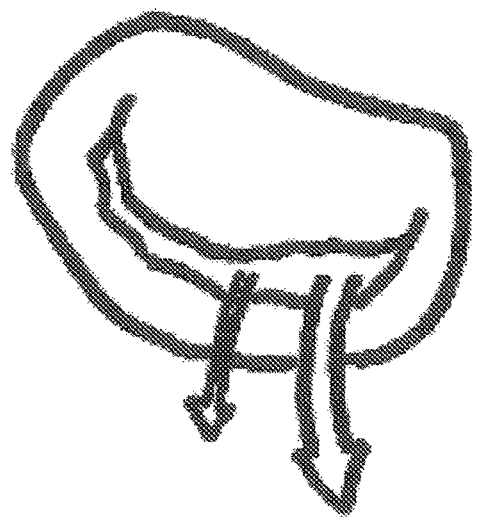

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

A method and apparatus are disclosed to perform mitral valve annuloplasty, such as for correcting mitral valve regurgitation. The method uses an anatomic approach to the mitral valve annulus with aortomitral continuity/fibrous trigone penetration from the left ventricular outflow tract, and a catheter apparatus is utilized which produces reduction and remodeling of the mitral valve annulus from that anatomic approach.

Successful annuloplasty requires firm anchoring to the central fibrous skeleton of the heart, and this anchoring has been absent from previous methods. Previous methods have additional problems with access to the mitral annulus. For example, surgical approaches to the left atrium may require a puncture of the interatrial septum, with the need for an additional device for closure of the defect created. In addition, the complex trabeculated internal surface of the left ventricle and the extensive array of chordae may interfere with surgical approaches involving the left ventricular cavity. Also, the coronary sinus is not sufficiently juxtaposed to the mitral annulus throughout its course to allow sufficient anchoring. Due to the anatomical approach of the method and apparatus disclosed herein, none of these additional problems are relevant.

The disclosed method involves mitral annuloplasty that is firmly anchored to the central fibrous skeleton of the heart. The method involves penetration of the tissue of the aortomitral continuity with a catheter apparatus from the aspect of the left ventricular outflow tract just below the aortic valve, penetration of the fibrous trigone tissue, and guided passage along the mitral annular heart tissue. The method includes traversing, by penetration, a broad segment of the anatomic anchoring zone tissue to an extent that is only feasible from the left ventricular outflow tract. Both the posteromedial circumference of the mitral annulus, through the right fibrous trigone, as well as the anterolateral circumference of the mitral annulus, through the left fibrous trigone, can be accessed for annuloplasty with the method disclosed herein. Additionally, since the method does not require access through the left atrial cavity, it can be used to approach a regurgitant mitral valve where the left atrium is small enough to hamper an open-heart surgical approach. Finally, because the method and apparatus disclosed herein do not leave exposed foreign material in a heart chamber with a low velocity of blood flow, there is no requirement for either short-term or long-term anticoagulation. Instead, the disclosed method and apparatus include retaining a very small amount of foreign material with a low structural profile in a portion of the heart where the velocity of blood flow is very high and where the need for anticoagulation is unlikely.

Figure 2:
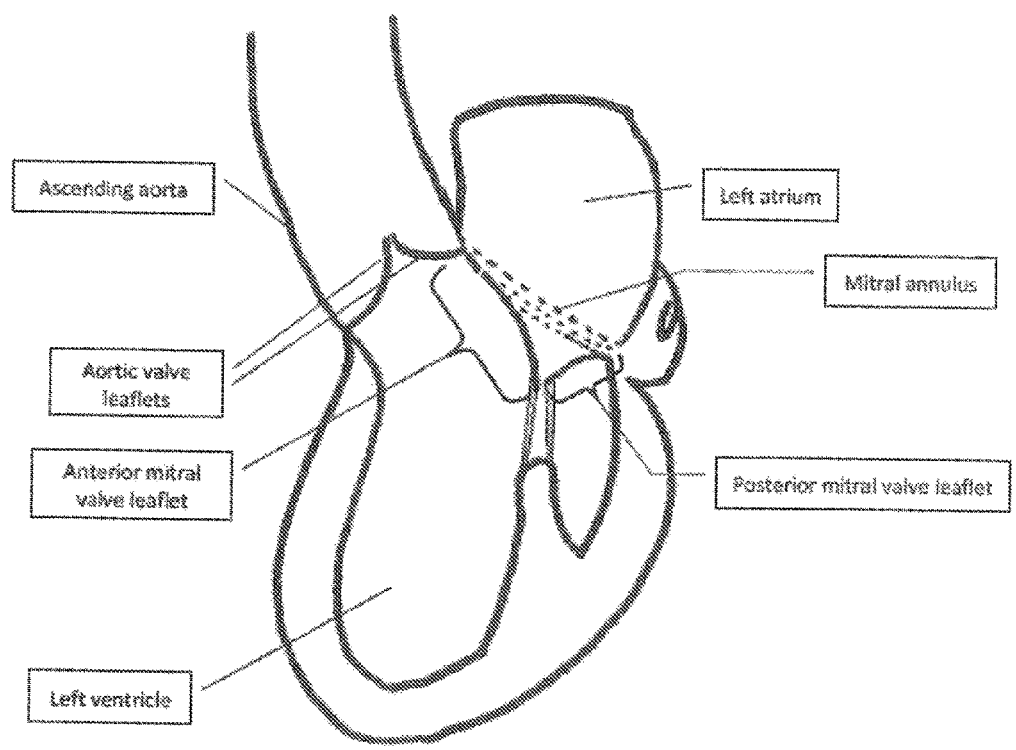
FIG. 2 illustrates the anatomy of the ascending aorta, the left ventricle, the left atrium, and the aortic and mitral valves in profile from a longitudinal anatomical section, wherein the dotted lines show the plane of the mitral valve annulus.

The disclosed method of mitral annuloplasty involves anchoring to the central fibrous skeleton of the heart at the right and left fibrous trigones. FIGS. 2-5 demonstrate this anatomic location in detail from different views. As a matter of background, FIG. 2 shows the anatomy of the ascending aorta, the left ventricle, the left atrium, and the aortic and mitral valves in profile from a longitudinal anatomical section. Although only the anterior and posterior mitral leaflets are visible in this particular section, the dotted lines show the plane of the mitral valve annulus. The continuity between the aortic valve and anterior mitral valve leaflet is demonstrated.

Figure 3:
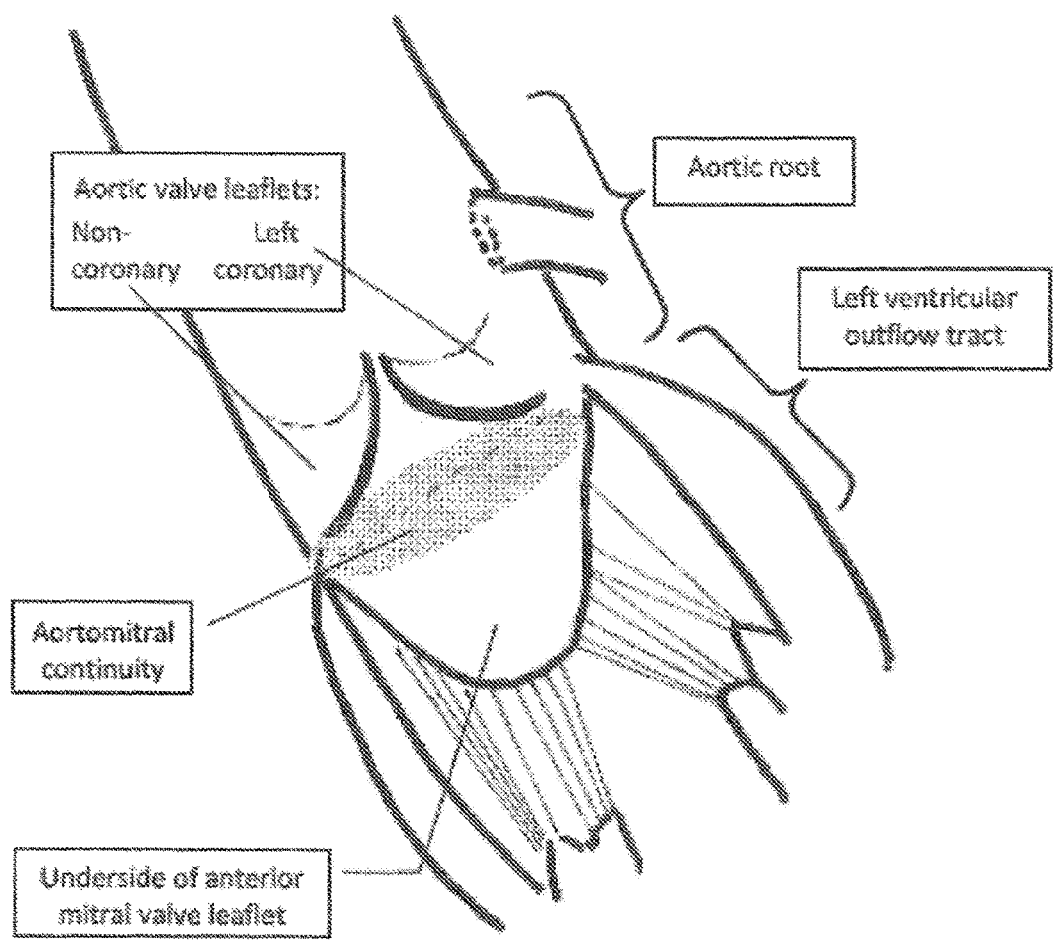
FIG. 3 illustrates a longitudinal section through the ascending aorta and the left ventricle, visualizing the anatomy from the inside of the aorta and from the inside of the left ventricle, wherein the aortomitral continuity is shown.

With reference to FIG. 3, the aortic valve and the anterior leaflet of the mitral heart valve are joined at the base or annulus by fibrous tissue (the anatomic site variably designated as "aortomitral fibrous continuity" or "aortomitral continuity" or "aortomitral curtain") in the area of the central fibrous skeleton of the heart. This area of junction includes the particularly thickened tissue known as the right and left fibrous trigones. FIG. 3 shows a longitudinal section through the ascending aorta and the left ventricle, visualizing the anatomy from the inside of the aorta and from the inside of the left ventricle. This initial portion of the aorta is the aortic root, and the adjoining part of the left ventricle is the left ventricular outflow tract. This view is facing the underside or ventricular aspect of the anterior mitral valve leaflet which is one boundary of this left ventricular outflow tract. This view shows part of the (stippled) area of fibrous continuity between the attachment of the left coronary leaflet of the aortic valve, the attachment of the noncoronary leaflet of the aortic valve, and the attachment of the anterior leaflet of the mitral valve.

Figure 4:
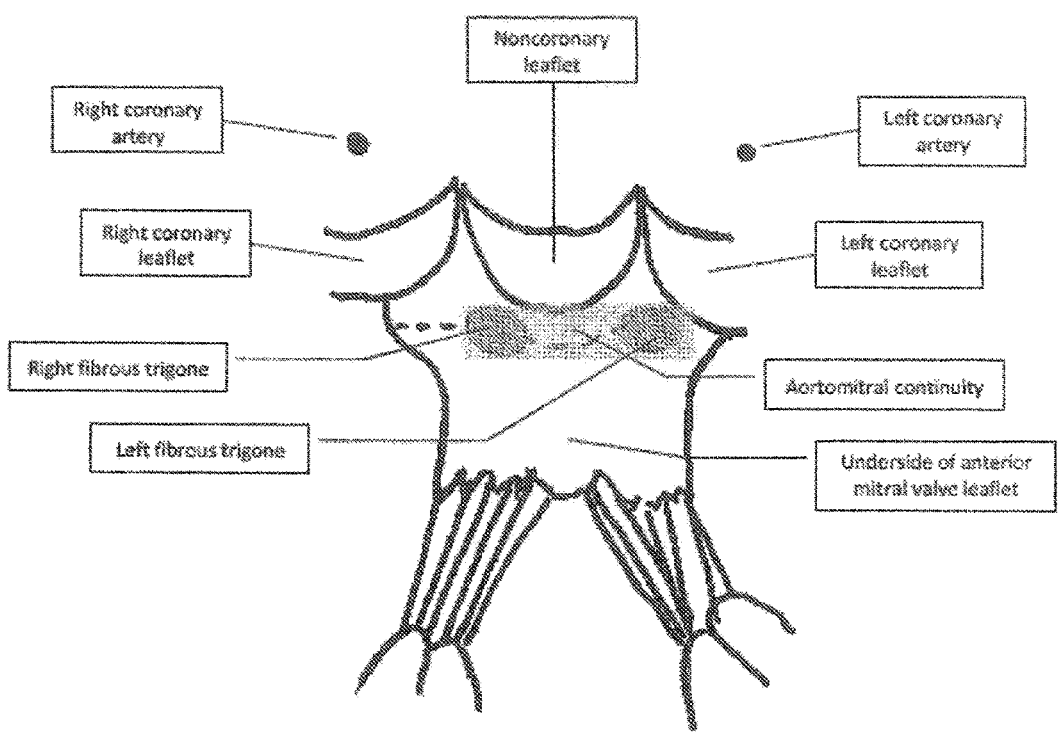
FIG. 4 illustrates the view of FIG. 3 as it would appear if the aorta was incised and unrolled.
Figure 5A:
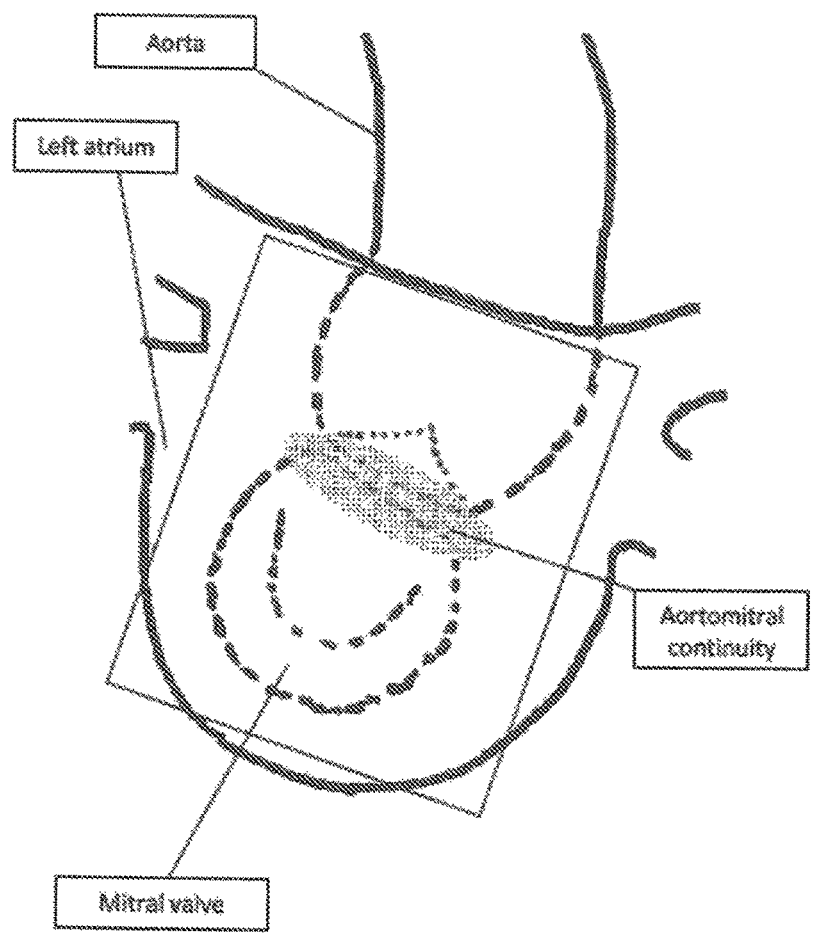
FIG. 5A illustrates the mitral value and aortic root from the posterior aspect, facing the plane of the mitral valve annulus.
Figure 5B:
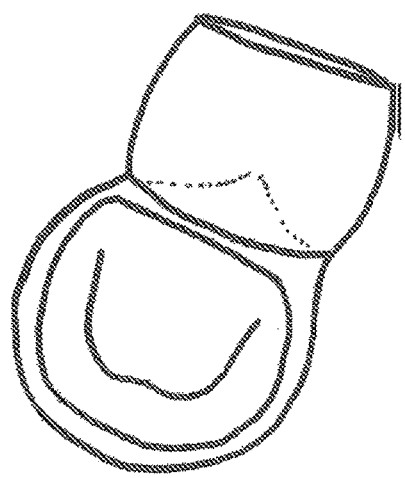
FIG. 5B is an inset view of FIG. 5A without the overlying left atrium.

The view of FIG. 4 is from the same projection as FIG. 3 but shows how the area would appear if the aorta was incised and "unrolled". The aortomitral fibrous continuity extends across the attachment of the noncoronary leaflet of the aortic valve, and includes the left and the right fibrous trigones. FIG. 5A shows the mitral valve and aortic root from the posterior aspect, facing the plane of the mitral valve annulus. There is a roughly 110 degree angle between the aortic root and the plane of the mitral valve, as shown in FIG. 2. The inset area (FIG. 5B) is shown without the overlying left atrium. The orientation in FIG. 5B will be used to demonstrate embodiments of the disclosed method and apparatus in subsequent figures.

Figure 6A:
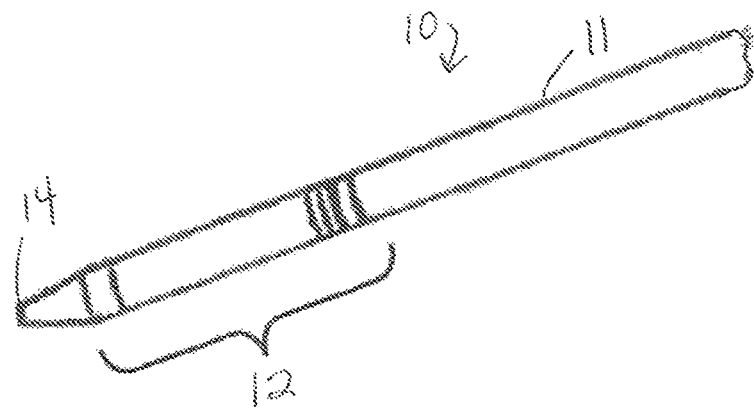
FIG. 6A illustrates a partially cut-away view of a catheter apparatus according to an embodiment including an ultrasound transducer.
Figure 6B:
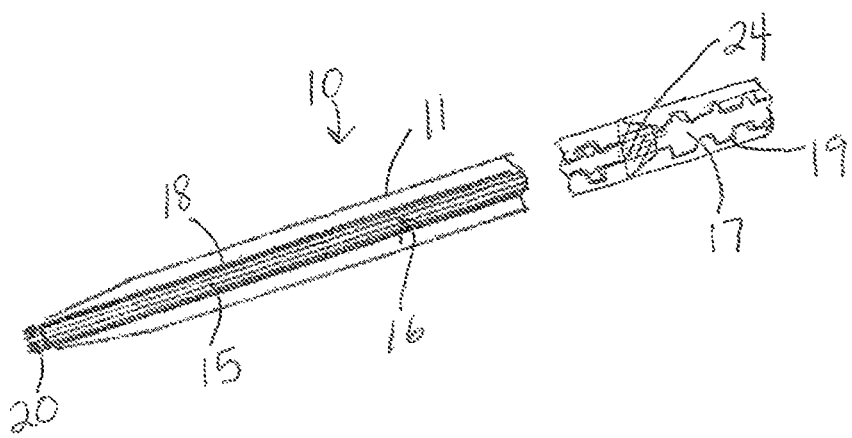
FIG. 6B is a longitudinal sectional, partially cut-away view of the catheter apparatus of FIG. 6A illustrating a tissue penetration member disposed within the catheter apparatus.
Figure 6C:
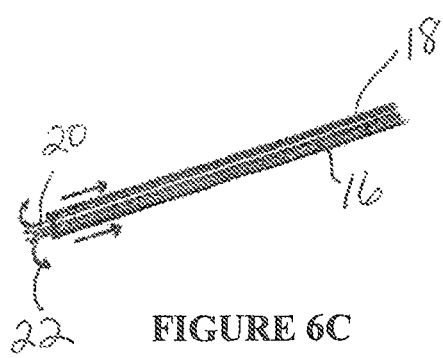
FIG. 6C is a view of the catheter apparatus of FIG. 6B with the housing removed to illustrate retraction of the sheath and deployment of the active fixation end of the tissue penetration member.

FIGS. 6A, 6B and 6C illustrate components of the catheter apparatus 10 according to an embodiment. The catheter apparatus 10 has a flexible housing 11, such as constructed from a plastic material, and may include an ultrasound transducer 12 at a distal end 14 thereof (FIG. 6A). In one embodiment, a 20-40 MHz ultrasound transducer 12 may be utilized to permit an imaging diameter of 1-2 cm, wherein the ultrasound transducer 12 is in electrical communication with an ultrasound monitor (not shown). In subsequent drawings, the ultrasound transducer 12 may be omitted for simplicity. In one embodiment, guidance of the catheter apparatus 10 may also utilize transesophageal echocardiography (TEE), such as three-dimensional TEE. The catheter apparatus 10 may be a single-use, disposable item, or components thereof may be constructed to be capable of sterilization and multiple uses.

The catheter apparatus 10 includes a tissue penetration member 16 contained within a flexible sheath 18, such as constructed from a plastic material (FIG. 6B). Via mechanical actuators (not shown) at the proximal end of the catheter apparatus 10, the tissue penetration member 16 is retractable within the catheter apparatus 10 and the sheath 18 is retractable within the catheter apparatus 10 and with respect to the tissue penetration member 16. In one embodiment, the tissue penetration member 16 may comprise a plurality of wires, such as constructed from a metallic material, in a bundle configuration terminating in a distal fixation end 20. However, other materials and configurations are contemplated, such as depending upon the stiffness desired. As best shown in FIG. 6C, the distal fixation end 20 may include a plurality of tines 22 such as, but not limited to, curved tines, hooks, or barbs or another shape to achieve tissue purchase. When the tissue penetration member 16 is contained within the sheath 18, the catheter apparatus 10 may be advanced within the tissue for tissue penetration. When the sheath 18 is retracted from the tissue penetration member 16 into the catheter apparatus 10, the distal fixation end 20 and its tines 22 may be configured to deploy radially outward, providing 360-degree fixation into the tissue. Deployment of the distal fixation end may occur automatically, such as due to outward biasing of the tines 22, or alternatively deployment may require initiation by a user, such as via a switch (not shown) on the catheter apparatus 10.

As best shown in FIG. 6B, the tissue penetration member 16 includes a washer or grommet 24, contained and deployed within the catheter apparatus 10. The grommet 24 may have a low profile configuration and may be constructed from any biocompatible material. In one embodiment, the grommet 24 is a one-way, directional device that is used for securing the calibrated amount of retraction of the tissue penetration member 16 as will be described below. The grommet 24 may be deployed along the tissue penetration member 16 by a mechanical actuator (not shown) at a proximal end of the catheter apparatus 10. In one embodiment, the tissue penetration member 16 has a distal portion 15 and a proximal portion 17, the proximal portion 17 including spaced protrusions 19. The protrusions 19 engage the grommet 24 to secure the tissue penetration member 16 as it is retracted through the grommet 24, such as at discrete intervals. Monitoring and imaging devices, such as the ultrasound transducer 12 and TEE, may be used to determine the distance "d" necessary to retract the tissue penetration member 16 through the grommet 24. A cutting actuator (not shown) may be deployed within the catheter apparatus 10 to amputate the tissue penetration member 16 adjacent to the grommet 24 per the disclosed method described below. In one embodiment, the tissue penetration member 16 may be amputated at its proximal portion 17 between protrusions 19, since the tissue penetration member 16 may have a reduced width at such locations.

The method includes obtaining access to the left and right fibrous trigone anchoring zones by passing the catheter apparatus 10 just beneath the aortic valve, penetrating the cardiac tissue structure known as the aortomitral continuity. From this approach through the left ventricular outflow tract, the method assures the broadest attachment to anchoring tissue that is anatomically feasible. After penetration of the fibrous trigone tissue, the method involves guided passage of the catheter apparatus 10 parallel to the mitral annular heart tissue.

In one embodiment, arterial access to the aorta is obtained by using a standard cardiac catheterization techniques, such as a needle and guide wire (Seldinger) technique, such as in a cardiac catheterization lab or hybrid operating room setting. Monitoring devices and methods, such as fluoroscopy and TEE, as well as monitoring with the catheter ultrasound transducer 12 may be utilized for guidance of tissue passage by the catheter apparatus 10 along the mitral valve annulus. Use of these imaging and monitoring modalities may vary depending upon the particular circumstances, and modification of the modalities used for localization and guidance is also contemplated.

Figure 7:
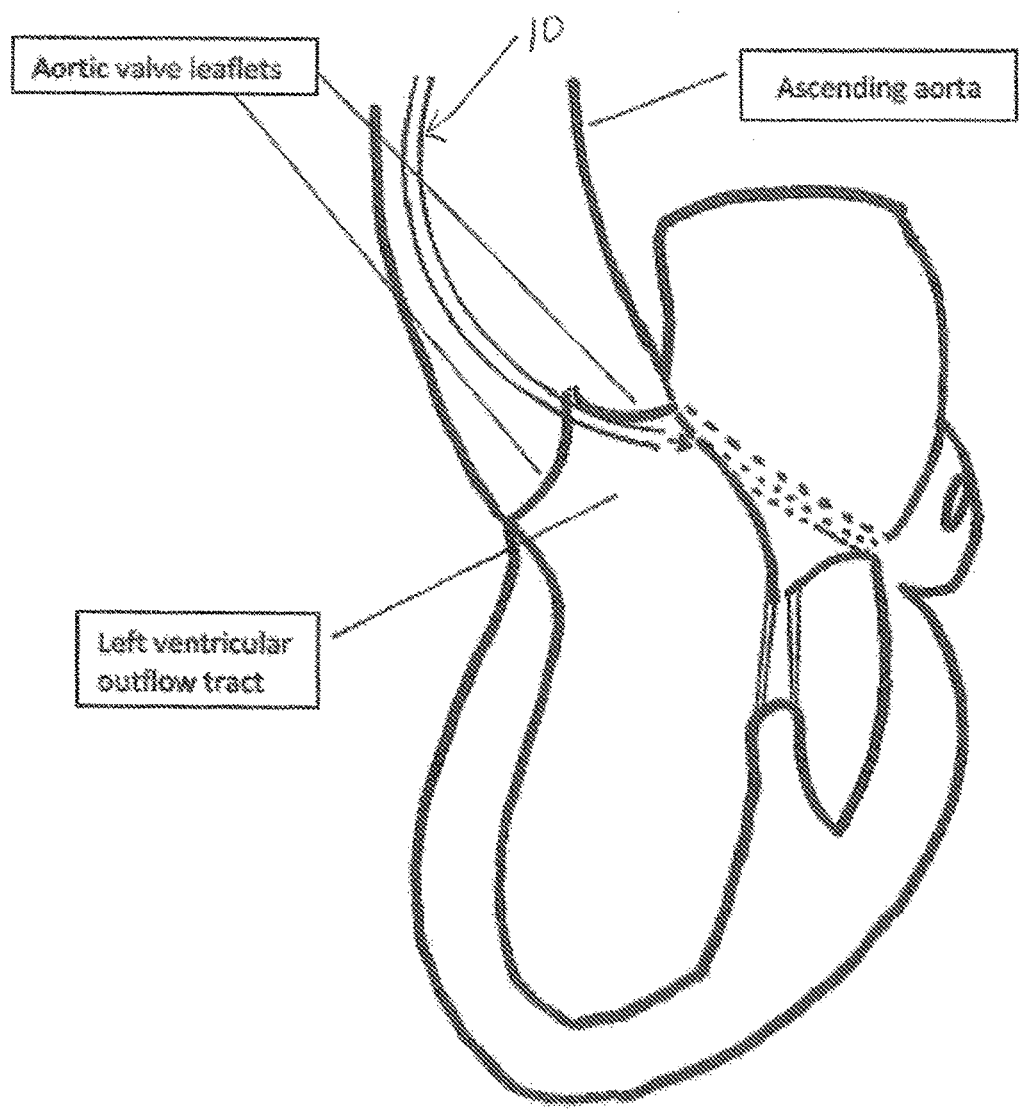
FIG. 7 illustrates the catheter apparatus passed into the ascending aorta, retrogradely across the aortic valve and into the left ventricular outflow tract, pointing toward the aortomitral continuity.

With reference to FIG. 7, after obtaining arterial access as described above, a guide catheter (not shown) is passed into the ascending aorta and with a guide wire (not shown) is passed retrogradely across the aortic valve into the left ventricular outflow tract. After the guide wire is removed, the catheter apparatus 10 is introduced through the arterial access and passed into the guide catheter to achieve access of the catheter apparatus 10 across the aortic valve. The longitudinal section in FIG. 7 shows the catheter apparatus 10 having been passed across the aortic valve and located in the left ventricular outflow tract, directed toward the aortomitral continuity (arrow).

Figure 8A:
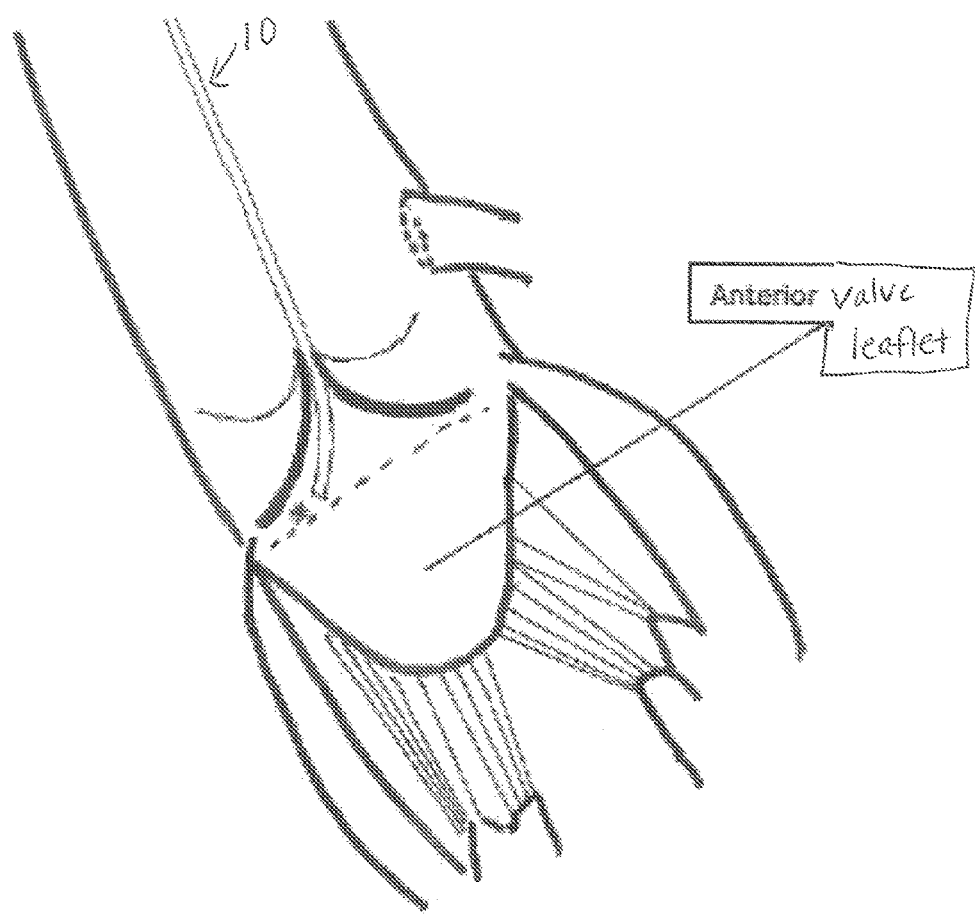
FIGS. 8A and 8B illustrate the catheter apparatus positioned in the left ventricular outflow tract at the aortomitral continuity from a longitudinal axis projection and facing the plane of the mitral valve annulus, respectively, where the catheter apparatus is being directed for annuloplasty along the posteromedial aspect of the mitral annulus and is thus positioned toward the right fibrous trigone.
Figure 8B:
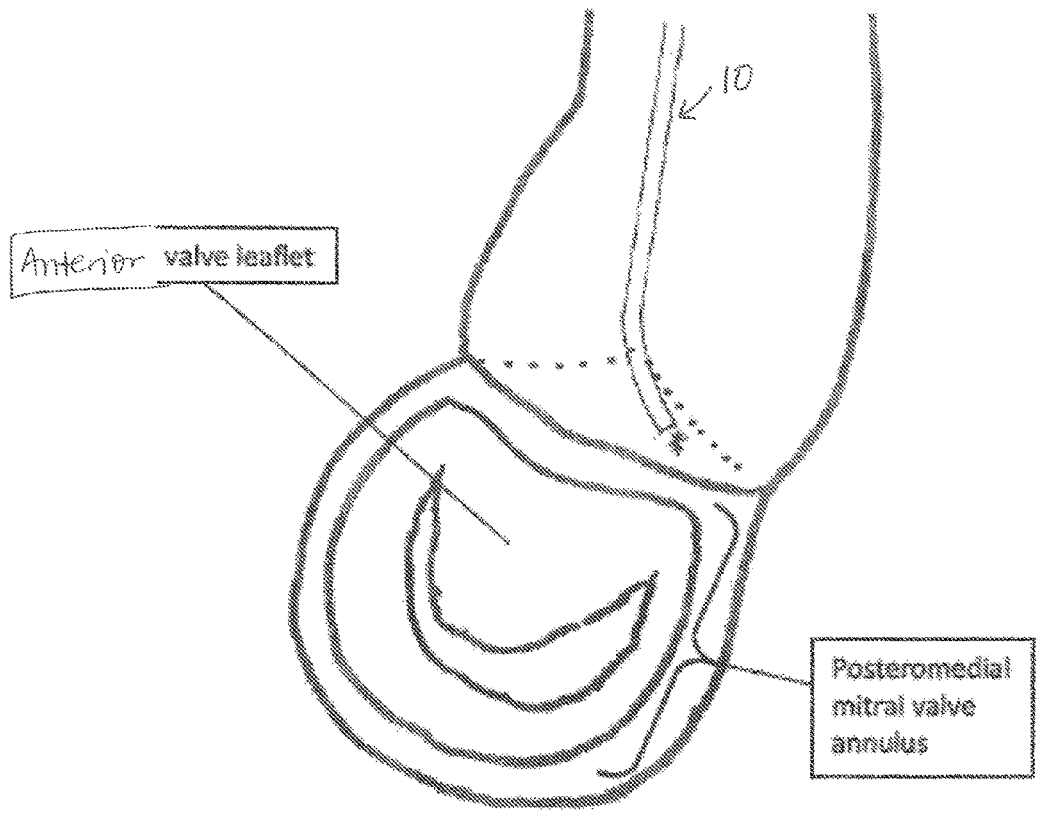

FIGS. 8A and 8B show the catheter apparatus 10 positioned and stabilized, such as with one or both of the ultrasound transducer 12 and TEE guidance, in the left ventricular outflow tract at the aortomitral continuity from two different projections, a longitudinal axis projection (FIG. 8A) and facing the plane of the mitral valve annulus (FIG. 8B). Depending on the particular pathoanatomy of mitral regurgitation in a patient, it may be necessary to perform annuloplasty at either the posteromedial half of the mitral annulus or the anterolateral half of the mitral annulus or both halves of the mitral annulus. The catheter apparatus 10 may be advanced along either the posteromedial aspect of the mitral annulus or anterolateral aspect of the mitral annulus, or both aspects with sequential applications. As a non-limiting example in these and subsequent figures, the catheter apparatus 10 is being directed for annuloplasty along the posteromedial aspect of the mitral annulus, therefore the catheter apparatus 10 is positioned toward and adjacent the right fibrous trigone (*).

Figure 9A:
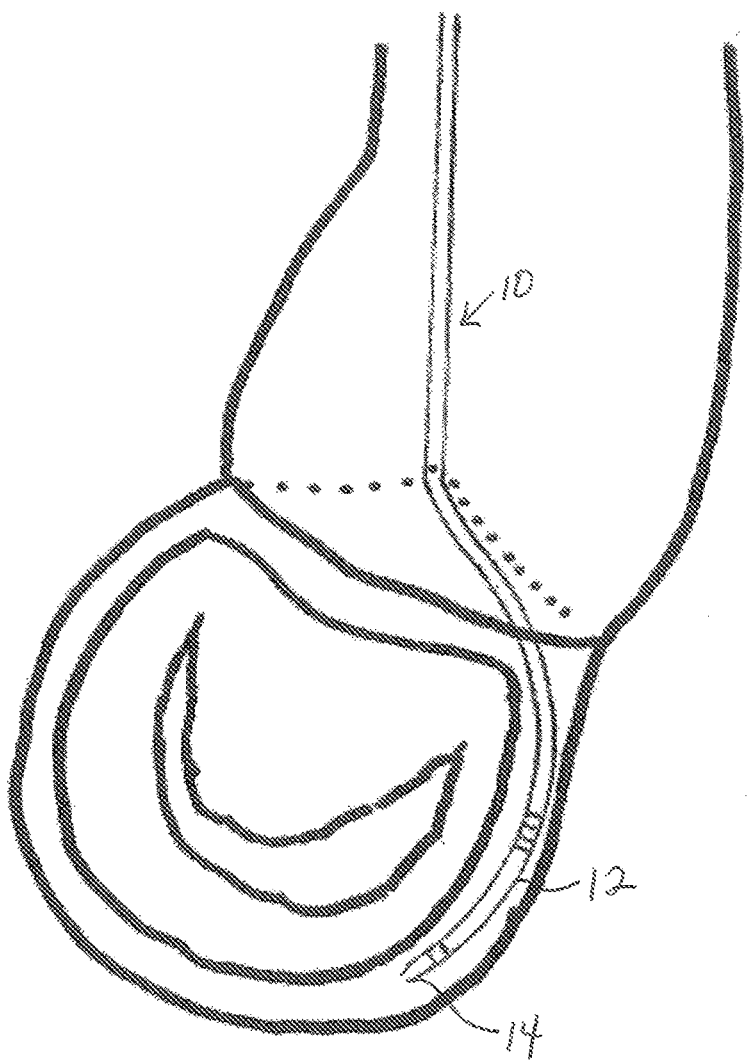
FIGS. 9A and 9B illustrate the catheter apparatus and its ultrasound transducer and tissue penetration member, respectively, having penetrated the aortomitral continuity tissue at the right fibrous trigone, then being passed through the tissue along the posteromedial mitral valve annulus.
Figure 9B:
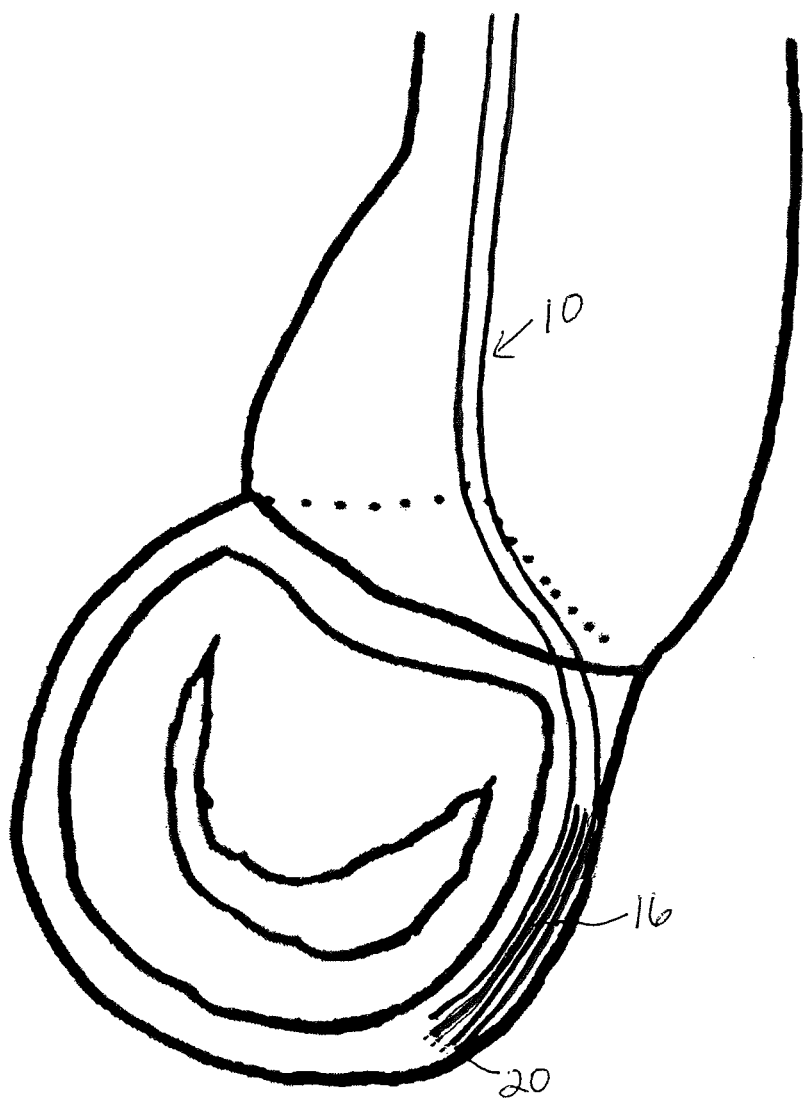

The catheter apparatus 10, having penetrated the aortomitral continuity tissue at the right fibrous trigone, is then passed through the tissue along the posteromedial mitral valve annulus as depicted in FIGS. 9A and 9B. For simplicity, FIG. 9A shows only the ultrasound transducer 12 of the catheter apparatus 10, and FIG. 9B shows only the tissue penetration member 16 of the catheter apparatus 10 enclosed within the sheath 18. The catheter apparatus 10 is advanced along the posteromedial mitral annulus, such as within 2-4 mm of the annulus.

Figure 10:
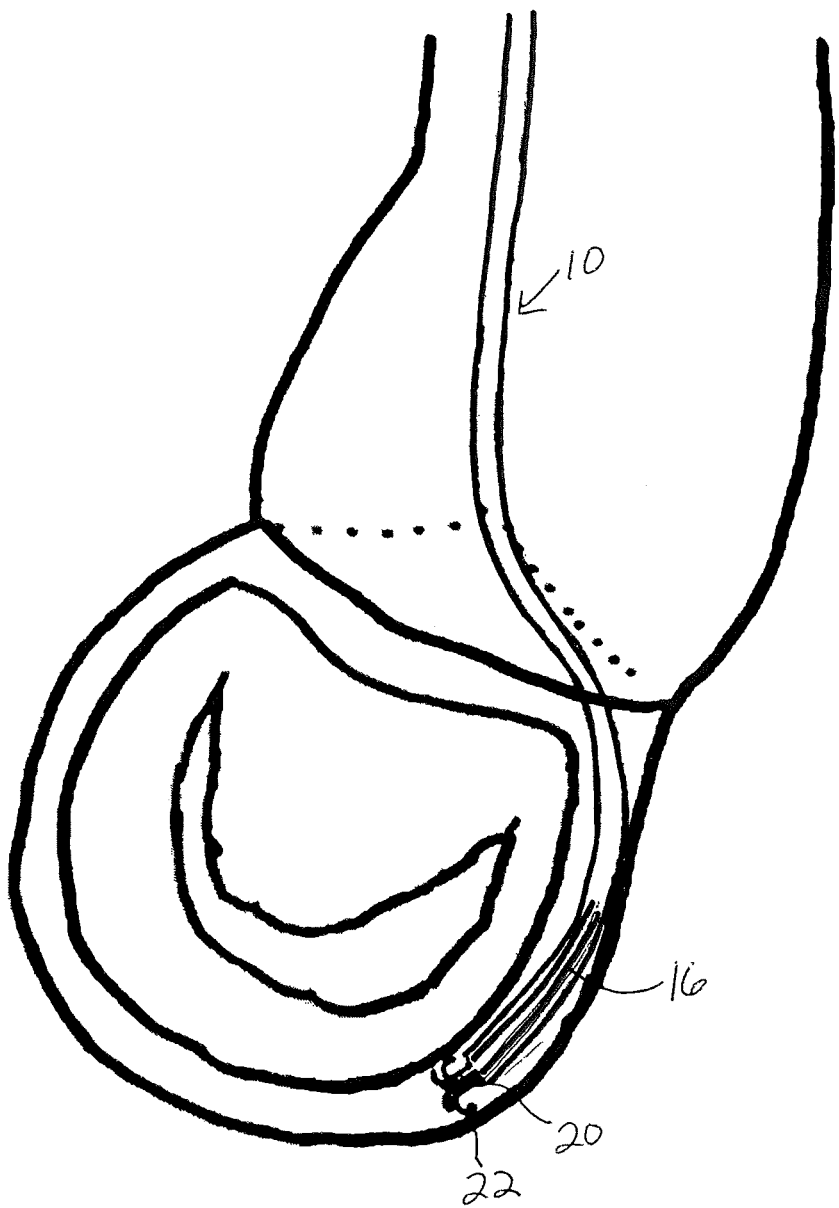
FIG. 10 illustrates the tissue penetration member with the sheath retracted in an active fixation configuration of the catheter apparatus.

After the catheter apparatus 10 is positioned at a desired location along the mitral annulus, the distal fixation end 20 is deployed. FIG. 10 depicts the sheath 18 retracted, exposing and deploying the tines 22 to engage tissue and provide an active fixation configuration of the catheter apparatus 10. If, at this stage, the catheter apparatus 10 needs to be repositioned before final deployment and tissue fixation, the sheath 18 can be passed distally over the tissue penetration member 16 and the catheter apparatus 10 moved.

Figure 11:
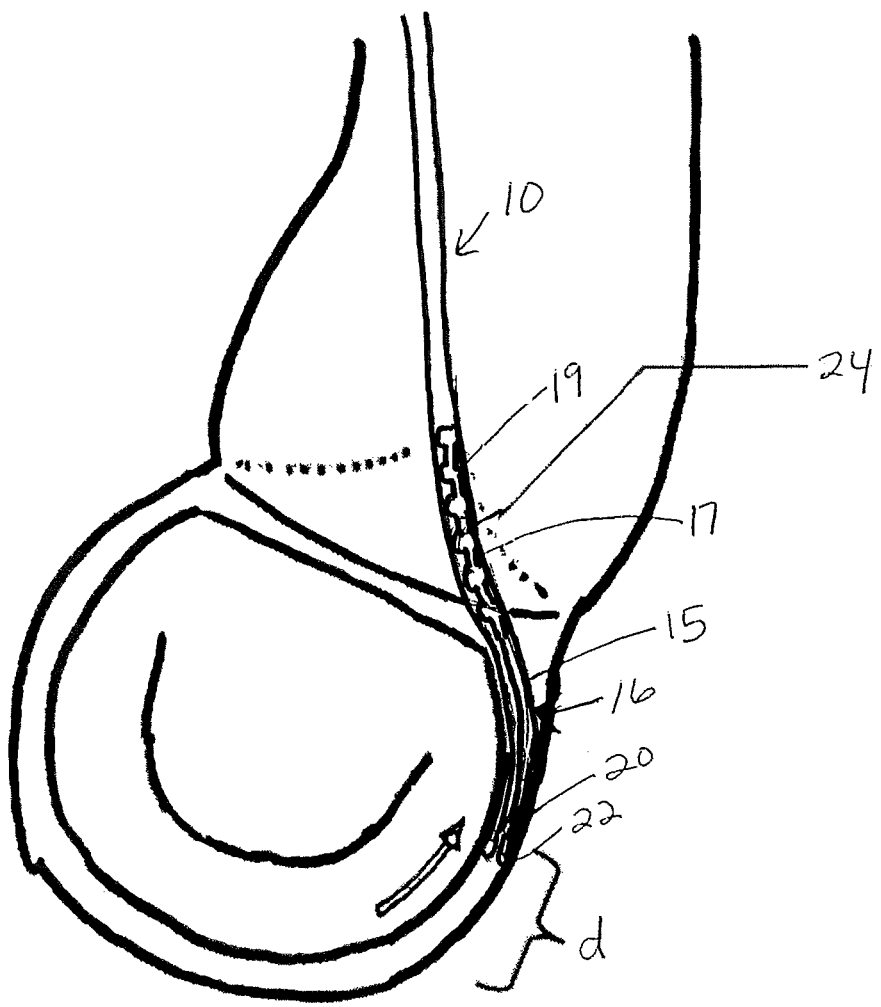
FIG. 11 illustrates deployment of a one-way grommet in-line with the tissue penetration member against the site of aortomitral continuity penetration in the left ventricular outflow tract and withdrawal of the tissue penetration member into the catheter apparatus a calibrated distance through the grommet to produce a calibrated compression of annular tissue anchored against the right fibrous trigone.

In order to achieve annuloplasty, the grommet 24 is deployed along and in-line with the tissue penetration member 16 from within the catheter apparatus 10 against the site of aortomitral continuity penetration in the left ventricular outflow tract (FIG. 11). Next, the tissue penetration member 16 is retracted into the catheter apparatus 10 and through the grommet 24 a measured or calibrated distance "d" required to correct the annular dimension, a process which may be aided using TEE guidance. The retraction produces a calibrated compression of malleable mitral annular tissue between a distal fixation site engaged by the distal fixation end 20 and the grommet 24 abutting the aortomitral continuity proximally, anchored against the right fibrous trigone. This tissue compression produces an anchored, stabilized reduction in the mitral annular dimension and remodeling of the annular shape in order to correct mitral regurgitation at this site.

Figure 12A:
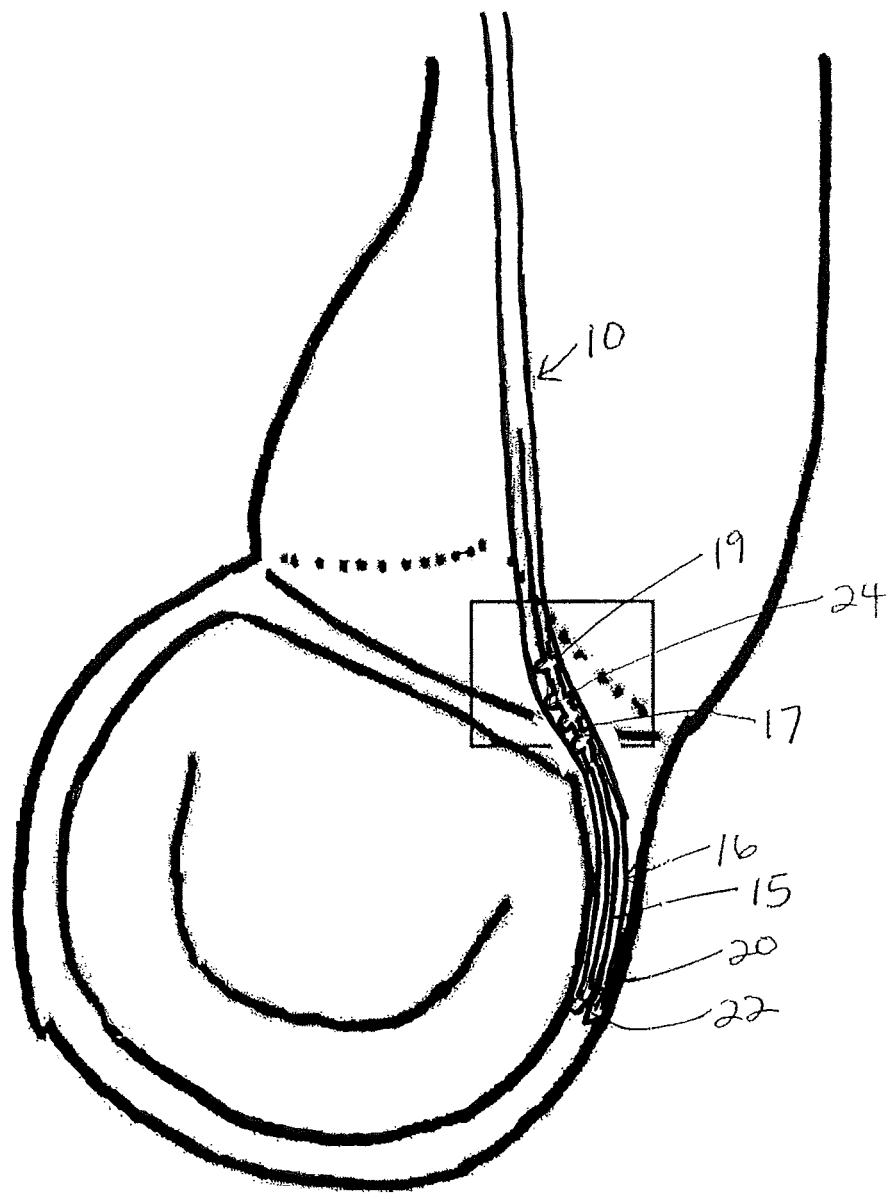
FIGS. 12A and 12B illustrate the completed catheter apparatus deployment and an inset view showing calibration of the distance for amputation of the tissue penetration member within the catheter apparatus, respectively.
Figure 12B:
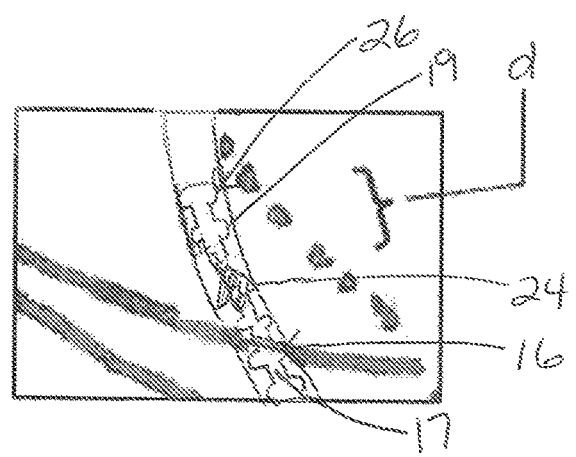
Figure 12C:
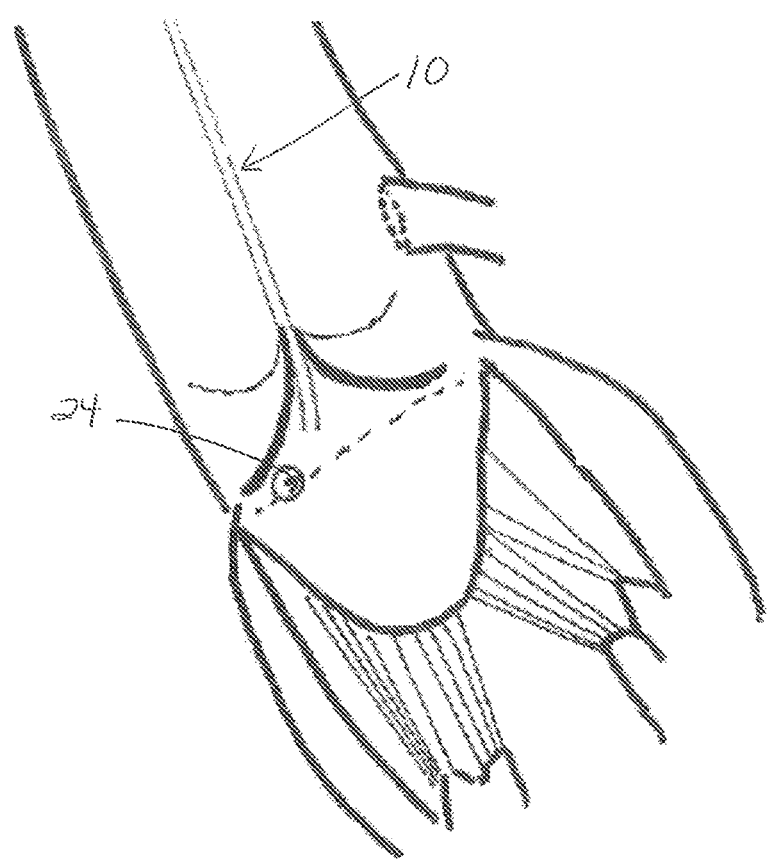
FIG. 12C illustrates a longitudinal axis projection of the catheter apparatus after amputation of the tissue penetration member.

FIG. 12A illustrates the completed deployment of the tissue penetration member 16 and the inset of FIG. 12B illustrates calibration of the distance "d" for amputation of the tissue penetration member 16 within the catheter apparatus 10. The tissue penetration member 16 is amputated on the left ventricular outflow tract aspect, beyond its proximal exit site from the grommet 24 to create a tail 26. The remainder of the proximal end of the tissue penetration member 16 may then be removed via the catheter apparatus 10. In one embodiment, the tissue penetration member 16 is amputated at a distance of approximately 2 mm beyond the grommet exit, but is not limited to this distance. The longitudinal axis projection of FIG. 12C shows the catheter apparatus 10 after amputation of the tissue penetration member 16. The catheter apparatus 10 is then withdrawn through the guide catheter.

Figure 13A:
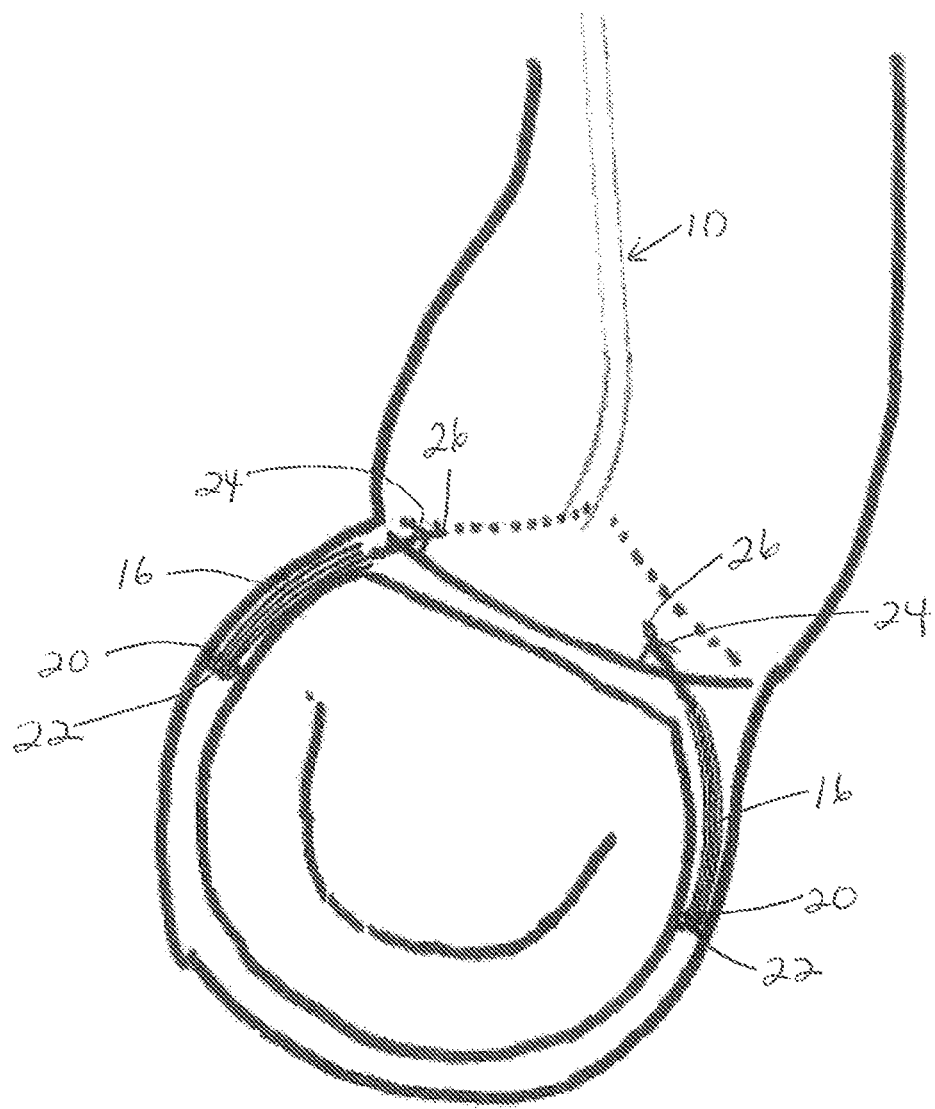
FIG. 13A illustrates deployment of another catheter apparatus to correct the anterolateral aspect of the mitral annulus with penetration through the left fibrous trigone.
Figure 13B:
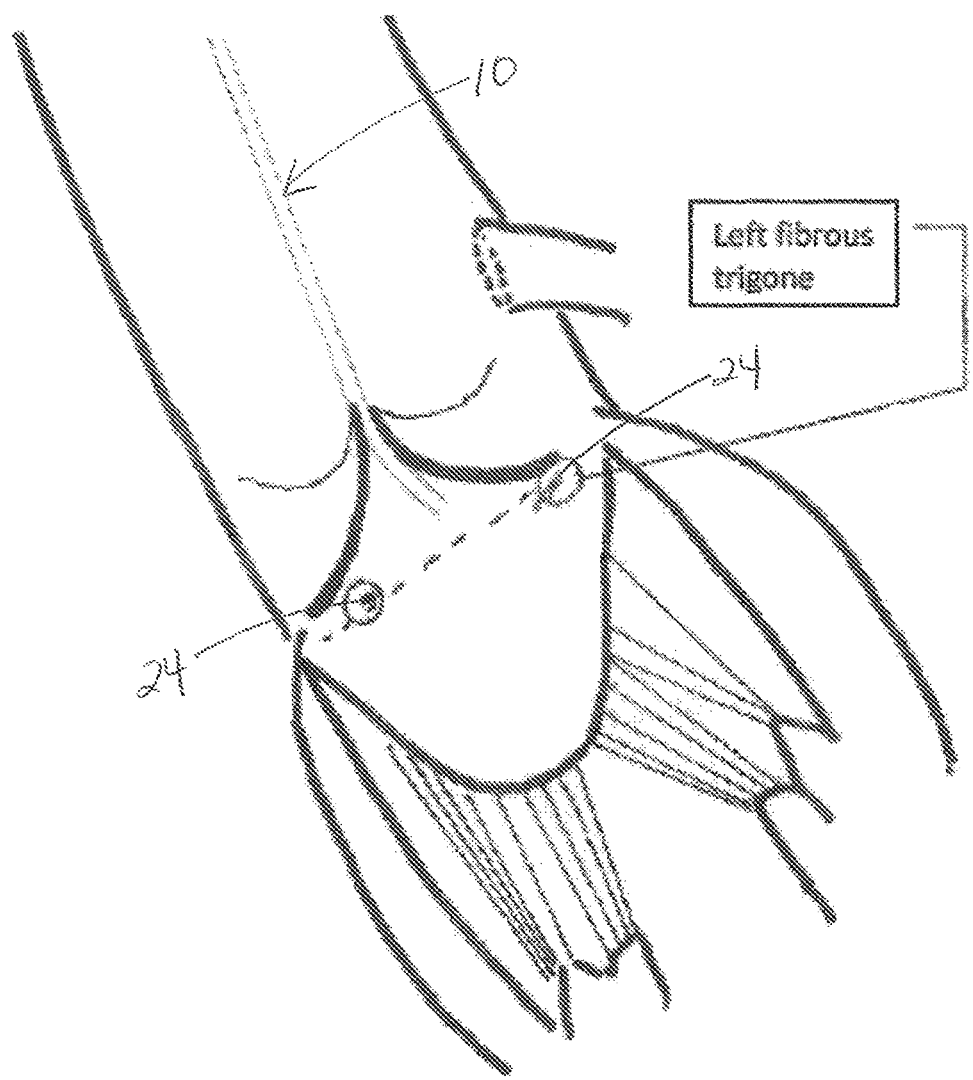
FIG. 13B illustrates a longitudinal axis projection of the completed appearance following the procedure of FIG. 13A facing the aortomitral continuity from the left ventricular outflow tract.

If only the posteromedial aspect of the mitral annulus requires treatment, the guide catheter can then be withdrawn. If the anterolateral aspect of the mitral annulus also requires treatment, then another catheter apparatus 10 is introduced through the guide catheter and the method repeated for penetration of the aortomitral continuity tissue through the left fibrous trigone and tissue passage along the anterolateral mitral annulus, as shown in FIG. 13A. The amount of annular reduction does not have to be identical on each aspect of the mitral annulus. Following treatment of the anterolateral aspect of the mitral annulus, the longitudinal axis projection of FIG. 13B shows the completed appearance facing the aortomitral continuity from the left ventricular outflow tract before withdrawing the catheter apparatus 10.

In an alternative embodiment, which may be dependent on the particular pathoanatomy of the mitral valve and aortomitral continuity, a left atrial approach may be used with initial tissue penetration of the catheter apparatus 10 at the mitral annulus, passage along the annular tissue, and exit through the aortomitral continuity. This embodiment would involve calibrated tissue compression between grommets 24 deployed at both the entry site of mitral annular penetration and the exit site in the left ventricular outflow tract. In addition, the method of aortomitral continuity/fibrous trigone penetration from the left ventricular outflow tract to approach the mitral valve annulus may have a different application other than the performance of mitral valve annuloplasty. Also, the catheter apparatus 10 may have an application for annuloplasty of the tricuspid valve.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A method for mitral valve annuloplasty, comprising:
   inserting a catheter apparatus across an aortic valve, the catheter apparatus including a tissue penetration member having a distal fixation end;
   penetrating an aortomitral continuity at tissue of a fibrous trigone with the catheter apparatus from a left ventricular outflow tract without entering a remainder of the left ventricle;
   advancing the catheter apparatus within annular tissue of a mitral valve annulus;
   deploying the distal fixation end to engage the annular tissue;
   retracting the tissue penetration member within the catheter apparatus to compress the annular tissue a desired distance for reduction of the annular tissue; and
   securing the retracted tissue penetration member to anchor the annular tissue reduction.

2. The method of claim 1, further comprising guiding and monitoring the catheter apparatus using ultrasound.

3. The method of claim 1, further comprising guiding and monitoring the catheter apparatus using transesophageal echocardiography (TEE).

4. The method of claim 1, wherein deploying the distal fixation end includes retracting a sheath surrounding the tissue penetration member.

5. The method of claim 1, wherein the distal fixation end includes tines, and deploying the distal fixation end includes deploying the tines radially outward to engage the annular tissue.

6. The method of claim 1, further comprising calibrating the desired distance for annular tissue reduction using TEE.

7. The method of claim 1, wherein securing the retracted tissue penetration member includes deploying a grommet along the tissue penetration member to secure the tissue penetration member.

8. The method of claim 7, wherein the tissue penetration member has a distal portion and a proximal portion, the proximal portion including spaced protrusions, the protrusions engaging the grommet to secure the tissue penetration member.

9. The method of claim 7, further comprising amputating the tissue penetration member proximal of the grommet.

10. The method of claim 1, wherein the annular tissue reduction is anchored at the aortomitral continuity and the fibrous trigone.

11. The method of claim 1, including at least one of penetrating a posteromedial circumference of the mitral valve annulus through a right fibrous trigone and penetrating an anterolateral circumference of the mitral valve annulus through a left fibrous trigone.

12. A method for mitral valve annuloplasty, comprising:
   inserting a catheter apparatus across an aortic valve, the catheter apparatus including a tissue penetration member having a distal fixation end, the tissue penetration member surrounded by a sheath;
   penetrating an aortomitral continuity at tissue of a fibrous trigone with the catheter apparatus from a left ventricular outflow tract without entering a remainder of the left ventricl;
   advancing the catheter apparatus within annular tissue of a mitral valve annulus;
   retracting the sheath to deploy the distal fixation end and engage the annular tissue;
   calibrating a desired distance for reduction of the annular tissue;
   retracting the tissue penetration member within the catheter apparatus to compress the annular tissue the desired distance; and
   deploying a grommet along the tissue penetration member to secure the retracted tissue penetration member and anchor the annular tissue reduction at the aortomitral continuity.

13. The method of claim 12, wherein the distal fixation end includes tines, and deploying the distal fixation end includes deploying the tines radially outward to engage the annular tissue.

14. The method of claim 12, further comprising amputating the tissue penetration member proximal of the grommet.

* * * * *

UNITED STATES PATENT AND TRADEMARK OFFICE
CERTIFICATE OF CORRECTION

PATENT NO. : 9,445,899 B2
APPLICATION NO. : 13/844117
DATED : September 20, 2016
INVENTOR(S) : Arcidi Page 1 of 1

It is certified that error appears in the above-identified patent and that said Letters Patent is hereby corrected as shown below:

In the Claims

Column 9, Lines 16-17, Claim 12:
After "remainder of the left"
Delete "ventricl" and
Insert -- ventricle --.

Signed and Sealed this
Third Day of January, 2017

Michelle K. Lee
*Director of the United States Patent and Trademark Office*